United States Patent [19]

Arora

[11] Patent Number: 5,360,794
[45] Date of Patent: Nov. 1, 1994

[54] DISUBSTITUTED AND DEOXY DISUBSTITUTED DERIVATIVES OF α-D-MANNOFURANOSIDES AND β-L-GULOFURANOSIDES HAVING ANTI-INFLAMMATORY AND ANTI-PROLIFERATIVE ACTIVITY

[75] Inventor: Sudershan K. Arora, Lansdale, Pa.

[73] Assignee: Medicarb Inc., Southampton, Pa.

[21] Appl. No.: 923,452

[22] Filed: Aug. 3, 1992

[51] Int. Cl.$^5$ ............................................. A61K 31/70
[52] U.S. Cl. ..................................... 514/25; 514/27; 514/32; 536/4.1; 536/17.2; 536/17.3
[58] Field of Search ................. 536/120, 4.1, 17.2, 536/17.3; 548/526; 514/25, 27, 32

[56] References Cited

U.S. PATENT DOCUMENTS

| | | | |
|---|---|---|---|
| 4,738,953 | 4/1988 | Gordon | 514/25 |
| 4,996,195 | 2/1991 | Ronsen et al. | 514/23 |
| 5,010,058 | 4/1991 | Ronsen et al. | 514/23 |

*Primary Examiner*—Marianne M. Cintins
*Assistant Examiner*—Phyllis Spivack
*Attorney, Agent, or Firm*—Oblon, Spivak, McClelland, Maier & Neustadt

[57] ABSTRACT

The compounds of the present invention are deoxy disubstituted or dideoxy disubstituted derivatives of α-D-mannofuranoside and β-L-gulofuranoside hexoses which exhibit anti-inflammatory and anti-proliferative activity. Pharmaceutical compositions containing the compounds and methods of treating inflammatory and-/or autoimmune disorders employing the compounds are disclosed.

8 Claims, No Drawings

DISUBSTITUTED AND DEOXY DISUBSTITUTED DERIVATIVES OF α-D-MANNOFURANOSIDES AND β-L-GULOFURANOSIDES HAVING ANTI-INFLAMMATORY AND ANTI-PROLIFERATIVE ACTIVITY

BACKGROUND OF THE INVENTION

1. Field of the Invention

The present invention relates to the novel design and synthesis of disubstituted or deoxydisubstituted α-D-mannofuranosides and β-L-gulofuranosides and intermediates for preparing these disubstituted derivatives. More specifically, this invention relates to alkyl or aralkyl 2,3-O-(1-methylethylidene)-α-D-mannofuranoside and β-L-gulofuranoside derivatives substituted at 1,5 or 1,6 - positions. It also relates to deoxy-hexofuranoside compounds wherein the chirality at position 5 is completely inverted. The compounds of this invention have anti-inflammatory and anti-proliferative activity and are useful for treating warm blooded animals and mammals with rheumatoid arthritis, osteoarthritis, scleroderma, systematic lupus erythematosus, autoimmune deficiency syndrome, atopic dermatitis, psoriasis and cancer. This invention also encompasses pharmaceutical compositions containing these disubstituted or deoxydisubstituted compounds and methods of treating inflammatory and/or autoimmune disorders.

2. Description of the Related Art

A glycoside is formed when the hydrogen atom of an anomeric hydroxyl group is replaced by a substituted or unsubstituted carbon atom. Typically, glycosides are formed either for group protection or as a part of a synthesis of a larger molecule. The Fischer method is particularly effective for synthesizing glycosides from unprotected reducing sugars and low molecular weight alcohols. Normally, after the glycoside is formed, various blocking methods are used to block or protect one or more of the hydroxyl groups. These blocking methods are described in U.S. Pat. Nos. 2,715,121, 4,056,322, 4,735,934, 4,996,195, and 5,010,058 the disclosure of which are incorporated herein by reference. The therapeutic activity of hexoses and their derivatives are also disclosed in the above application.

A well known derivative of α-D-glucose having beneficial therapeutic properties is Amiprilose HCl, 1,2-O-isopropylidene-3-O-3'-(N', N'-dimethylaminopropyl)-α-D-glucofuranose. This compound, which is in the late Phase III clinical trials, has anti-inflammatory activity and demonstrated utility in managing the signs and symptoms of rheumatoid arthritis. More generally, these type of compounds have activity as immunomodulators, and therefore have a therapeutic effect on other autoimmune disorders such as psoriasis, eczema, or lupus (U.S. Pat. No. 5,010,058).

Unfortunately, while some of the prior art monosaccharide derivatives have shown beneficial therapeutic activity, high doses of these compounds, such as Amiprilose HCl, are often needed to be effective and produce the desired results. Therefore, the prior art derivatives are difficult to prescribe orally. Because therapy for inflammatory and autoimmune disorders is often midterm or longterm, there is a need to develop potent, non-toxic compounds which can be orally administered to promote ease of treatment and patient compliance.

OBJECTS OF THE PRESENT INVENTION

An object of the present invention, therefore, is to provide new compounds that exhibit significantly greater potency than available compounds, which may be preferrably orally administered. The compounds of the present invention have attained these objects and it is believed that the present compounds act by a different mechanism than Amiprilose HCl. They are more selective in their activity.

Another object of the present invention is to provide novel carbohydrate compounds that exhibit significantly greater potency for cancer treatment (particularly melonoma and colon cancer). There is no example available in the literature wherein hexoses, particularly mannofuranoside and gulofuranoside derivatives, are used for treating cancer patients (particularly for treating melonoma and colon cancer).

It is, therefore, an object of the present invention to provide novel disubstituted or deoxydisubstituted hexofuranoside compounds and compositions which exhibit anti-inflammatory and antiproliferation activity. It is also an object of the present invention to provide novel compounds and compositions which are useful in the treatment of animals and mammals having anti-inflammatory and/or auto-immune disorders. It is a further object of this invention to provide a novel, simple, efficient and one step-process for preparing alkyl or aralkyl or heterocyclic alkyl 2,3-O-(1-methylethylidene)-α-D mannofuranoside and β-L-gulofuranoside compounds.

SUMMARY OF THE INVENTION

In order to achieve the above-mentioned objects and in accordance with the purposes of the invention as embodied and broadly described herein, there is provided mannofuranosides and gulofuranosides having the following formula (1):

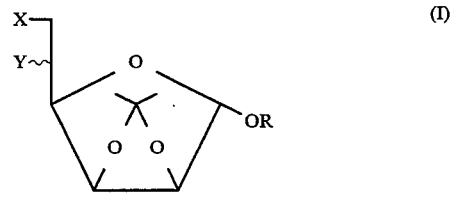

wherein

R is nonyloxypropyl, phenylpropyl, 4-(1-pyrolidinyl) butyl, 2-octyne, and $C_7$–$C_{15}$ alkyl;

$X = R^1$ or H;

$Y = OH$, $OR^2$ or $R^1$ wherein $R^1$ is OH, pyrrolidinyl, piperidinyl, morpholinyl, hexamethyleneimino, aminopropylpyrrolidinyl, aminoethylpyrrolidinyl, aminoethylmorpholinyl, aminoethylpiperidinyl, amino-$C_7$–$C_{15}$ alkyl or $C_7$–$C_{15}$ alkyl;

$R^2$ is dimethylaminopropyl, $C_7$–$C_{15}$ alkyl;

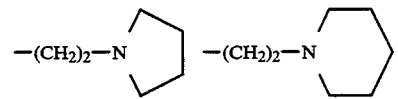

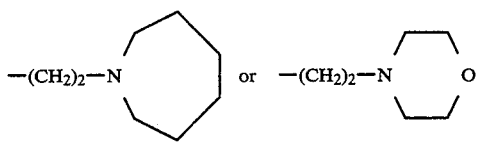

provided that X=R¹ when Y=OH and
X=H when Y=OR² or R¹
where (∿) indicates that the substituent is on the same side with respect to position 6 (mannofuranoside) or the other side (gulofuranoside)

The present invention also provides a pharmaceutical composition containing an effective amount of one or more of the above compounds, and a method of treating an inflammatory or autoimmune disorder comprising administering an effective amount of a compound described above or a physiological acceptable acid-addition salt thereof with a pharmaceutical acceptable carrier.

The mannofuranoside and gulofuranoside compounds of the present invention exhibit greater potency in terms of their activity (Con A, fibroblast, and Mixed Lymphocyte Response) than known glucofuranose compounds, such as Amiprilose HCl. The present compounds also show significant activity for the treatment of colon and melonoma cancer. These novel compounds provide decreased skin cell proliferation and inhibition of the proliferative response of splenic T-lymphocytes to known mitogen. Since T-lymphocytes are the immune cells that regulate immune responses, the compounds of the present invention can be used for treating warm blooded animals and mammals with inflammatory and/or autoimmune disorders such as rheumatoid arthritis, oesteoarthritis, psoriasis, atopic dermatitis, scleroderma, systemic lupus erythematosus, autoimmune defficiency syndrome, and cancer (melonoma and colon). Also the compounds of the present invention can be administered internally or externally.

The present invention is also directed to a one step process for preparing fully blocked glycosides such as alkyl or aralkyl 2,3 5,6-di-O-(1-methylethylidine)-α-D-mannofuranoside which can be used as a precursor in preparing the compounds of the present invention. This process comprises adding suitable alcohol such as alkyl alcohol or aralkyl alcohol to a suspension of D-mannose in acetone containing a catalytic amount of an acid such as concentrated sulfuric acid.

To block hexoses as in the present case, D-mannose is treated with an aldehyde or ketone, it may be blocked at 2,3 and 5,6 positions leaving only one hydroxyl group at the anomeric position free to derivatize. The anomeric hydroxyl group is then reacted with an alcohol in the presence of an acid catalyst to form glycoside. There is no example available thus far wherein glycosides of deoxy or dideoxy disubstituted α-D-mannofuranose and β-L-gulofuranose derivatives are used as a therapy for inflammatory or autoimmune disorders. Therefore, this invention describes the synthesis of novel compounds having anti-proliferative and anti-inflammatory activity.

DETAILED DESCRIPTION OF THE INVENTION

The compounds of the present invention may be prepared by the following general reaction schemes:

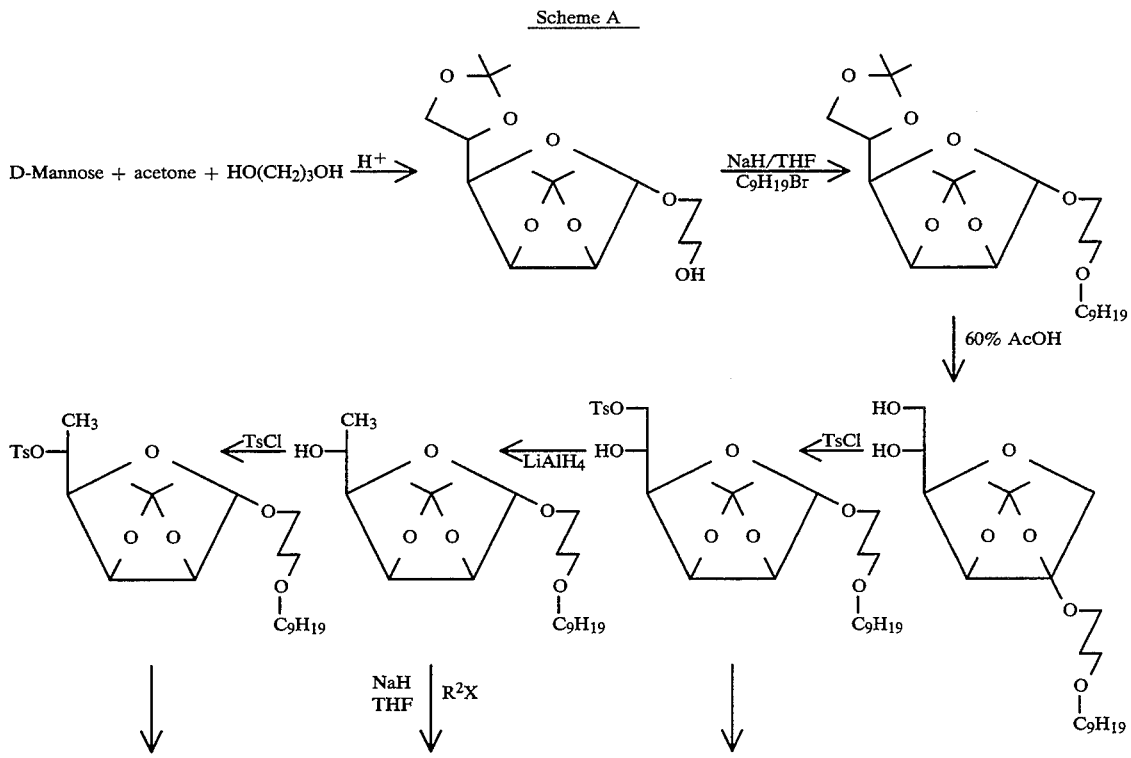

-continued
Scheme A

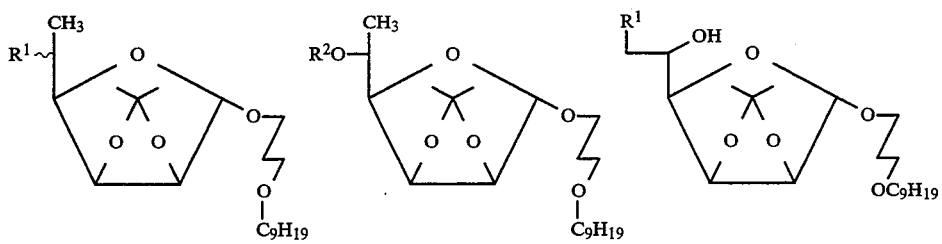

where R[1] is, for example, pyrrolidinyl, piperidinyl, morpholinyl, hexamethyleneimino, aminopropylpyrrolidinyl; R[2] is, for example, is dimethylaminopropyl, hexamethyleneiminoethyl, N-ethylpyrrolidine, N-ethylpiperidine, and $C_7$–$C_{15}$ alkyl chain; and X is Cl or Br so as to provide the compounds as described above, where aminopropylpyrrolidinyl is

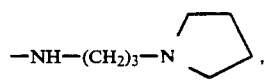

Specific compounds of the present invention which may be prepared according to scheme A include:

1. n-Nonyloxypropyl 2,3-O-(1-methylethylidene)-α-D-mannofuranosidese
2. n-Nonyloxypropyl 6-deoxy-2,3-O-(1-methylethylidene)-α-D-mannofuranoside
3. n-Nonyloxypropyl 2,3-O-(1-methylethylidene)-6-deoxy-pyrrolidinyl-α-D-mannofuranoside
4. n-Nonyloxypropyl 2,3-O-(1-methylethylidene)-6-deoxy-6-piperidinyl-α-D-mannofuranoside
5. n-Nonyloxypropyl 2,3-O-(1-methylethylidene)-6-deoxy-6-morpholinyl-α-D-mannofuranoside
6. n-Nonyloxypropyl 2,3-O-(1-methylethylidene)-6-deoxy-6-hexamethyleneimino-α-D-mannofuranoside
7. n-Nonyloxypropyl 2,3-O-(1-methylethylidene)-6-deoxy-6-aminothylpyrrolidinyl-α-D-mannofuranoside
8. n-Nonyloxypropyl 2,3-(1-methylethylidene)-6-deoxy-6-aminoheptyl-α-D-mannofuranoside
9. n-Nonyloxypropyl 2,3-O-(1-methylethylidene)-6-deoxy-5-O-nonyl-α-D-mannofuranoside
10. n-Nonyloxypropyl 2,3-O-(1-methylethylidene)-6-deoxy-5-O-(N,N-dimethylaminopropyl)-α-D-mannofuranoside
11. n-Nonyloxypropyl 2,3-O-(1-methylethylidene)-6-deoxy-5-O-hexmethyleneiminoethyl-α-D-mannofuranoside
12. n-Nonyloxypropyl 2,3-O-(1-methylethylidene)-6-deoxy-5-O-(N'-ethylpyrrolidinyl)-α-D-mannofuranoside
13. n-Nonyloxypropyl 2,3-O-(1-methylethylidene)-6-deoxy-5-O-(N'-ethylpiperidinyl)-α-D-mannofuranoside
14. n-Nonyloxypropyl 2,3-O-(1-methylethylidene)-5,6-dideoxy-5-aminononyl-β-L-gulofuranoside
15. n-Nonyloxypropyl 5,6-dideoxy-2,3-O-(1-methylethylidene)-5-pyrrolidinyl-β-L-gulofuranoside
16. n-Nonyloxypropyl 5,6-dideoxy-2,3-O-(1-methylethylidene)-5-piperidinyl-β-L-gulofuranoside.
17. n-Nonyloxypropyl 5,6-dideoxy-2,3-O-(1-methylethylidene)-5-hexamethyleneimino-β-L-gulofuranoside.

Scheme B

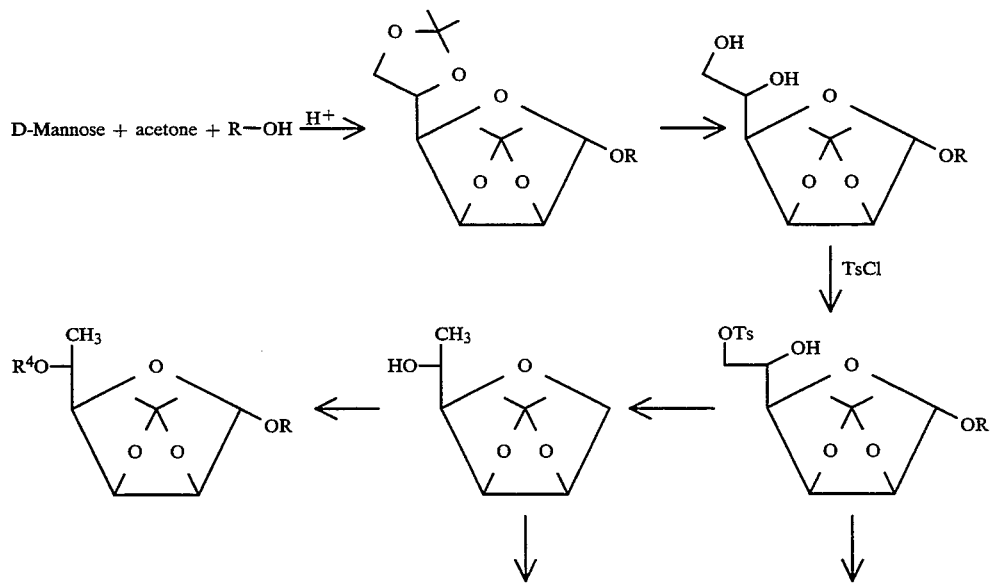

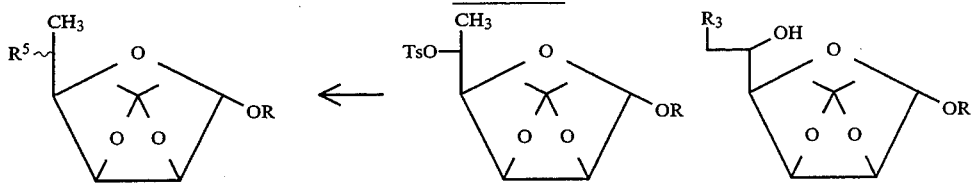

Scheme B where R, for example, is $C_7$–$C_{15}$ alkyl $C_6H_5(CH_2)_3$, 2-octyne-1-ol, 4-(1'-pyrrolidinyl)butyl; $R^3$ and $R^5$ are, for example, pyrrolidinyl, $C_7$–$C_{15}$ aminoalkyl, morpholinyl, piperidinyl, aminoethylpyrrolidinyl, aminopropylpyrrolidinyl, aminoethylpiperidinyl, aminoethylmorpholinyl, hexamethyleneimino; $R^4$ is, for example, $C_7$–$C_{15}$ alkyl, dimethylaminopropyl, ethylpyrrolidinyl, ethylpiperidinyl, ethylmorpholinyl, hexamethyleneiminoethyl, etc. so as to produce the compounds described above.

Specific compounds of the present invention which may be prepared according to scheme B include:

18. Phenyloprophyl 2,3-O-(1-methylethylidene)-α-D-mannofuranoside.
19. Phenylpropyl 6-deoxy 2,3-O-(1-methylethylidene)-α-D-mannofuranoside.
20. Phenylpropyl 6-deoxy 2,3-O-(1-methylethylidene)-6-pyrrolidinyl-α-D-mannofuranoside.
21. Phenylpropyl 6-deoxy 2,3-O-(1-methylethylidene)-6-heptylamino-α-D-mannofuranoside.
22. Phenylpropyl 6-deoxy 2,3-O-(1-methylethylidene)-6-aminopropylpyrrolidinyl-α-D-mannofuranoside.
23. Phenylpropyl 5,6-dideoxy 2,3-O-(1-methylethylidene)-5-heptylamino-β-L-gulofuranoside.
24. Phenylpropyl 5,6-dideoxy 2,3-O-(1-methylethylidene)-5-pyrrolidinyl-β-L-gulofuranoside.
25. Phenylpropyl 5,6-dideoxy 2,3-O-(1-methylethylidene)-5-amino ethylpyrrolidinyl-β-L-gulofuranoside.
26. Phenylpropyl 6-deoxy 2,3-O-(1-methylethylidene)-5-O-3'-(N'N'-dimethylamino-n-propyl)-α-D-mannofuranoside.
27. Phenylpropyl 6-deoxy 2,3-O-(1-methylethylidene)-5-O-(N'-ethylpyrrolidinyl)-α-D-mannofuranoside.
28. 2'-Octyne 2,3-O-(1-methylethylidene)-α-D-mannofuranoside.
29. 4'-(1-Pyrrolidinyl)butyl 2,3-O-(1-methylethylidene)-α-D-mannofuranoside A simple and efficient one step process for the synthesis of fully blocked glycosides such as alkyl or substituted alkyl, aralkyl, or heterocyclic alkyl 2,3;5,6-di-O-(1-methylethylidene)-α-D-mannofuranoside is described herein, which starts by reacting D-mannose with acetone and a suitable alcohol in the presence of a catalytic amount of concentrated sulfuric acid.

It is to be understood that several derivatives of the present compounds described herein may be prepared by prior art techniques and used in a therapeutic composition and the method of the invention. For example free amino compounds are basic and form organic and inorganic acid salts and the resulting salts are useful in the therapeutic composition and method of invention. Any physiologically tolerable anion is suitable to produce such salts. These may be prepared by the usual prior art techniques, such as suspending the compound in water and then adding exactly one equivalent of the desired organic acid or mineral acid. Example of suitable acids include hydrochloric acid, sulfuric acid, nitric acid, maleic acid, benzoic acid, tartaric acid, acetic acid, p-aminobenzoic acid, oxalic acid, succinic acid, gluconic acid, and glucoronic acid. The neutral solution of the resulting salt is subjected to rotary evaporation under diminished pressure to the volume necessary to assure precipitation of the salt upon cooling, which is then filtered and dried. The salts of the present invention may also be prepared strictly under nonaqueous conditions, for example, dissolving the free amine in dry ether and adding exactly one equivalent of the desired acid in ether. Stirring the solution at 0°–5° C. causes the precipitation of the amine salt which are filtered, washed with ether and dried. The amine salts are often preferred for use in formulating the therapeutic compositions of the invention as they are crystalline and relatively more stable and non-hygroscopic. The amine salts are also better adapted for intramuscular injection than are the free amines.

Because of their valuable pharmacological properties, the compounds of the present invention may be administered to human patients or animals either orally, topically, rectally, internasally, or by parenteral administration. When the therapeutic composition is to be administered orally, the compounds of the present invention may be admixed with one or more prior art fillers, excipients and/or binders (e.g., starch) and a disintegrator, if desired, and the mixture pressed into a tablet convenient for oral administration. Capsules may also be filled with the powdered therapeutic composition and administered orally. Alternatively, a water solution of the amine salt or suspension of the therapeutic composition may be admixed with a flavored syrup and administered orally. A salt of the free amine is usually preferred where the compound is administerd by intramuscular injection.

The pharmaceutical compositions of the present invention are preferably produced and administered in dosage units, each unit containing as active component a certain base amount of at least one compound described above and/or at least one of its physiologically acceptable acid addition salts. The dosage may be varied over extremely wide limits as the compounds are effective at low dosage levels and are relatively free of toxicity. The compounds may be administered in the minimum quantity which is therapeutically effective, and the dosage may be increased as desired up to the maximum dosage tolerated by the patient. In the case of an animal or human, the effective dose to treat autoimmune and or inflammatory disorders can range from 1 to 50 mg per kilogram of body weight per day, and preferably in an amount of about 2 to 30 mg per kilogram per day, over a period required for the treatment. In the case of in vitro testing, the effective amount to achieve 50% inhibition of the cultured cells ranged from 1 to 100 μg per ml of the cultured medium, preferably 2 to 50 μg.

The following examples demonstrate the synthesis of compounds according to this invention and illustrate the beneficial therapeutic properties of these compounds. The examples described are illustrative, and are not to be considered as limitative in any manner.

EXAMPLES

Various solvents, such as acetone, methanol, pyridine, tetrahydrofuran, dimethylsulfoxide, ether, hexanes, and ethylacetate were dried using various drying reagents by the procedures known in the art. Wet solvents gave poor yields of the products or their intermediates. IR spectra were recorded as nujol mulls or a thin neat film on a Beckman instrument using sodium chloride plates. PMR, CMR, and various 2D spectra were recorded on a Varian XL-300 MHz instrument using TMS as an internal standard reference. CIMS were obtained on a Finnigan MAT-4510 mass spectrometer equipped with an INCOS data system. Generally, a direct exposure probe was used and methane was used as a reagent gas (0.35 mm Hg, 120° C. source temperature).

EXAMPLE 1

Preparation of n-Nonyloxypropyl 6-deoxy-2,3-O-(1-methylethylidene)-6-pyrolidinyl-α-D-mannofuranoside Step 1: 3'-Hydroxypropyl 2,3;5,6-di-O-(1-methylethylidene)-α-D-mannofuranoside:

A mixture of D-mannose (40 g), acetone (300 ml), 1,3-propanediol (40 g) containing conc. $H_2SO_4$ (5 ml) was refluxed for 5 hours. The reaction mixture was then neutralized with triethylamine and the solvents removed. The residue was dissolved in either (250 ml), washed with water (1×50 ml), a saturated solution of sodium bicarbonate (2×50 ml), a saturated solution of sodium bicarbonate (2×50 ml), a brine (1×50 ml), and the organic layer was dried ($MgSO_4$), filtered, and the solvent removed using rotary evaporator. The crude product obtained was purified by flash chromatography using 10% Ether in Hexane. The yield of the pure compound, 3'-hydroxypropyl 2;3;5,6-di-O-(1-methylethylidene)-α-D-mannofuranoside was (84%). CIMS: 319 (M+1).

Step 2: Nonyloxypropyl 2,3;5,6-di-O-(1-methylethylidene)-α-D-mannofuranoside:

Sodium hydride (60%, 4.4 g), made free of oil by washing with hexane, was taken in a 1-liter round bottomed flask and added anhydrous THF (150 ml). The reaction flask was cooled at 5°–10° C. and to this was added a solution of 3'-hydroxypropyl 2,3;5,6-di-O-(1-methylethylidene)-α-D-mannofuranoside (31.8 g; 0.1 mole) in dry THF (150 ml), dropwise, with stirring, over a period of 30 minutes, under nitrogen. The mixture was stirred at the same temperature for 1 hour and then 1-bromononane (0.12 mole) was added dropwise. After the complete addition of 1-bromononane, the ice bath was removed and the mixture refluxed for 3 hours. The flask was then brought to ambient temperature, and the solvents removed. The residue was dissolved in ether (500 ml), washed with brine (2×50 ml), the organic layer dried ($MgSO_4$) and the solvent removed. The crude product so obtained was purified by flash chromatography using silica gel and eluting with ether:hexane (10:90) to yield the pure compound (40.5 g; 91.9%). CIMS: 445 (M+1).

Step 3: Nonyloxypropyl 2,3-O-(1-methylethylidene)-α-D-mannofuranoside:

A mixture of nonyloxypropyl 2,3;5,6-di-O-(1-methylethylidene)-α-D-mannofuranoside (40 g) in acetic acid (50%, 200 ml) was heated at 50°–55° C. for 8 hours. Acetic acid was then stripped off using diminished pressure and the residue was purified using column chromatography (15% Ether in hexane). The yield of the pure product was 82%. CIMS: 405 (M+1).

Step 4: Nonyloxypropyl 2,3-O-(1-methylethylidene)-6-p-toluenesulfonyl-α-D-mannofuranoside:

Nonyloxypropyl 2,3-O-(1-methylethylidene)-α-D-mannofuranoside (16 g) was dissolved in anhydrous pyrridine (100 ml) and cooled the flask at 0°–5° C. Stirring was started and added a solution of p-toluenesulfonylchloride (7.54 g; 1 equivalent) dropwise, over a period of 15 minutes. After 10 hours of stirring, pyridine was removed under diminished pressure and the residue dissolved in ethylacetate (250 ml). The organic layer washed with a saturated solution of sodium bicarbonate (2×50 ml), brine (1×50 ml), dried under $MgSO_4$, filtered, and solvent removed. The crude product was purified by column chromatography using ether:hexane (35:65) to yield, Nonyloxypropyl 2,3-O-(1-methylethylidene)-6-O-p-toluenesulfonyl-α-D-mannofuranoside, in 78% yield. CIMS: 549 (M+1).

Step 5: Nonyloxypropyl-6-deoxy-2,3-O-(1-methylethylidene)-6-pyrrolidinyl-α-D-mannofuranoside:

A mixture of Nonyloxypropyl 2,3-O-(1-methylethylidene)-6-O-p-toluenesulfonyl)-α-D-mannofuranoside (4 g) and pyrrolidine (6 ml) was heated at 70°–80° C. for 2 hours. The excess pyrralidine was then removed using rotary evaporator and added ether (50 ml). The solid salt formed was filtered off and the filtrate washed with a saturated solution of sodium bicarbonate (1×10 ml), brine (1×10 ml), organic layer dried ($MgSO_4$), filtered and solvent removed. The product was purified by column chromatography using silica gel G and eluting with ether:hexane (40:60). The yield of the pure product, Nonyloxypropyl 6-deoxy-2,3-O-(1-methylethylidene)-6-pyrrolidinyl-α-D-mannofuranoside, was 88%. CIMS: 458 (M+1).

EXAMPLE 2 n-Nonyloxypropyl 6-deoxy-2,3-O-(1-methylethylidene)-6-piperidinyl-α-D-mannofuranoside:

A mixture of nonyloxypropyl 2,3-O-(1-methylethylidene)-6-O-p-toluenesulfonyl-α-D-mannofuranoside (as obtained in step 4 of example 1) was treated with piperidine in exactly the same way as described in step 5 of example 1. The yield of the purified product was 86%. CIMS: 472 (M+1).

EXAMPLE 3 n-Nonyloxypropyl 6-deoxy-2,3-O-(1-methylethylidene)-6-morpholinyl-α-D-mannofuranoside:

The title compound was prepared in the same manner as described in step 5 of example 1 by reacting nonyloxypropyl 2,3-O-(1-methylethylidene)-6-O-p-toluenesulfonyl-α-D-mannofuranoside with morpholine. The yield of the purified product was 82%. CIMS: 474 (M+1).

EXAMPLE 4 n-Nonyloxypropyl 6-deoxy-2,3-O-(1-methylethylidene)-6-hexamethyleneimino-α-D-mannofuranoside:

The title compound was obtained in 82% yield by treating the 6-toluenesulfonyl compound (as obtained in step 4 of example 1) with hexamethyleneimine by exactly the same procedure as described in step 5 of example 1. CIMS: 486 (M+1).

EXAMPLE 5 n-Nonyloxypropyl 6-deoxy-2,3-O-(1-methylethylidene)-6-1'-(3'-aminopropyl)pyrrolidinyl-α-D-mannofuranoside:

This compound was prepared in exactly the same way as described in example 4 except 1-(3-aminopropyl)-pyrrolidine was used in place of hexamethyleneimine. The yield of the pure product was 81%. CIMS: 515 (M+1).

EXAMPLE 6

Nonyloxypropyl 5,6-dideoxy-2,3-O-(1-methylethylidene)-5-pyrrolidinyl-β-6-gulofuranoside:

Step 1: Nonyloxypropyl 6-deoxy-2,3-O-(1-methylethylidene)-α-D-mannofuranoside:

To a stirred suspension of lithium aluminum hydride (1.42 g) in anhydrous THF (100 ml) was added a solution of Nonyloxypropyl 2,3-O-(1-methylethylidene)-6-p-toluenesulfonyl-α-D-mannofuranoside (10.96 g) in dry THF (100 ml), dropwise over a period of 15 minutes at 0°–5° C. After the complete addition of the compound, the reaction mixture was stirred at the same temperature for 3 hours. The excess LiAlH₄ was then decomposed by the careful addition of 2 ml H₂O followed by 2 ml of 15% sodium hydroxide solution. The reaction mixture was filtered through celite, washed with ether (100 ml) and the solvents removed using rotary evaporator. The residue was dissolved in ether (150 ml), washed with water 20 ml), ether layer dried (MgSO₄), filtered and solvent removed. The product obtained (94% yield) was found to be sufficiently pure and showed a single homogeneous spot on tlc, and hence was used as such for the next step. CIMS: 389 (M+1).

Step 2: Nonyloxypropyl 6-deoxy-2,3-O-(1-methylethylidene)-5-p-toluenesulfonyl-α-D-mannofuranoside:

To a stirred solution of nonyloxypropyl 6-deoxy-2,3-O-(1-methylethylidene)-α-D-mannofuranoside (14.52 g; 0.03 mole) in pyridine (100 ml) was added p-toluenesulfonyl chloride (2.5 equivalents) in one portion. The reaction mixture was stirred at ambient temp. for 16 hours. It was then worked up by the same procedure as described in Example 1, step 4. The yield of the pure product (after column chromatography) was 81%. CIMS: 534 (M+1).

Step 3: Nonyloxypropyl 5,6-dideoxy-2,3-O-(1-methylethylidene)-5-pyrrolidinyl-β-L-gulofuranoside:

This compound was prepared by exactly the same procedure, by reacting Nonyloxypropyl 6-deoxy-2,3-O-(1-methylethylidene)-5-p-toluenesulfonyl)-β-D-mannofuranoside (4 g) with pyrrolidine (6 ml) at a reflux temperature for 4 hours, as described in step 5 of example 1. The yield of the pure product was 79%. CIMS: 442 (M+1).

EXAMPLE 7

Nonyloxypropyl 5,6-dideoxy-2,3-O-(1-methylethylidene)-5-piperidinyl-β-L-gulofuranoside:

The title compound was prepared in 86% yield by reacting nonyloxypropyl 6-deoxy-2,3-O-(1-methylethylidene)-5-P-toluenesulfonyl-α-D-mannofuranoside with piperidine by the same procedure as described for step 3 in example 6. The product was purified by column chromatography using silica gel G and eluted with ether:hexane (45:65). CIMS: 456 (M+1).

EXAMPLE 8

Nonyloxypropyl 5,6-dideoxy-2,3-O-(1-methylethylidene)-5-nonylamino-β-L-gulofuranoside:

The treatment of nonyloxypropyl 6-deoxy-2,3-O-(1-methylethylidene)-5-p-toluenesulfonyl-α-D-mannofuranoside (4 g) with 1-aminononane (6 ml) at 90°–100° C. for 6 hours gave the title compound in 80% yield. The procedure adopted was the same as described for example 7. CIMS: 514 (M+1).

EXAMPLE 9 n-Nonyloxypropyl 5,6-dideoxy-2,3-(1-methylethylidene)-5-hexamethyleneimino-β-L-gulofuranoside:

This compound was obtained in 84% yield by exactly the same manner as described in example 8 except that hexamethyleneimine was used in place of 1-aminononane. CIMS: 470 (M+1).

EXAMPLE 10 n-Nonyloxypropyl 6-deoxy-2,3-O-(1-methylethylidene)-5-O-nonyl-α-D-mannofuranoside:

Sodium hydride (60%, 4.4 g) was made free of oil by washing with hexane. To this was added anhydrous THF (150 mL) and the flask was cooled to 0°–5° C. A solution of n-nonyloxypropyl 6-deoxy-2,3-O-(1-methylethylidene)-α-D-mannofuranoside (obtained in step 1, example 6) (38.8 g; 0.1 mole) in dry THF (160 mL) was added dropwise to the above suspension, with stirring, over a period of 30 minutes. The mixture was stirred at the same temperature for 1 hour and then 1-bromononane (0.12 mole) was added dropwise. After the complete addition of 1-bromononane, the ice bath was removed and the mixture was refluxed for 4 hours. The reaction flask was then brought to ambient temperature and the solvent removed using rotary evaporator. The residue was dissolved in ethylacetate (500 mL), washed with brine (2×50 mL), the organic layer dried (MgSO₄), filtered and the solvent removed. The crude product so obtained was purified by flash chromatography using silica gel and eluting with 5% ethylacetate in hexane to yield the pure product in 92% yield. CIMS: 515 (M+1).

EXAMPLE 11 n-Nonyloxypropyl 6-deoxy-2,3-O-(1-methylethylidene)-5-O-3'-(N',N'-dimethylamino-n-propyl)-α-D-mannofuranoside:

The title compound was prepared in 87% yield exactly in the same manner as described in example 10 by reacting n-nonyloxypropyl 6-deoxy-2,3-(1-methylethylidene)-α-D-mannofuranoside with dimethylamino-n-propylchloride in the presence of sodium hydride in tetrahydrofuran. CIMS: 474 (M+1).

EXAMPLE 12 n-Nonyloxypropyl 6-deoxy-2,3-O-(1-methylethylidene)-5-O-hexamethyleneiminoethyl-α-D-mannofuranoside:

This compound was prepared in 89% yield in exactly the same manner as described in example 10 except that hexamethyleneiminoethyl chloride was used in place of 1-bromononane. CIMS: 514 (M+1).

EXAMPLE 13 n-Nonyloxypropyl 6-deoxy-2,3-O-(1-methylethylidene)-5-O-2'-(N'-ethylpyrrolidinyl)-α-D-mannofuranoside:

The title compound was obtained in 93% yield by reacting nonyloxypropyl 6-deoxy-2,3-O-(1-methylethylidene)-α-D-mannofuranoside with sodium hydride and 1-(2-chloroethyl)pyrrolidine. The procedure used was same as described in example 10. CIMS: 486 (M+1).

EXAMPLE 14 n-Nonyloxypropyl 6-deoxy-2,3-O-(1-methylethylidene)-5-O-2'-(N'-ethylpiperidinyl-α-D-mannofuranoside:

This compound was prepared in 90% yield by treating 6-deoxy compound with sodium hydride and 1-(2-chloroethyl piperidine). The procedure used was same as described in example 10. CIMS: 500 (M+1).

EXAMPLE 15

Phenylpropyl 6-deoxy-2,3-O-(1-methylethylidene)-6-heptylamino-α-D-mannofuranoside:

Step 1: Phenylpropyl 2,3;5,6-di-O-(1-methylethylidene)-α-D-mannofuranoside:

A mixture of D-Mannose (180 g; 1.0 mole) and 3-phenyl-1-propanol (272 g; 2.0 mole) in acetone (1 L) containing concentrated sulfuric acid (30 ml) was refluxed for 6 hours. The progress of the reaction was monitored by tlc. After 6 hours of reaction time, the mixture was neutralized with triethylamine to a ph of 7.0. The solvents were then stripped using rotary evaporator and the residue dissolved in ether (500 ml). The ethereal layer was washed with water (1×50 ml), a saturated solution of sodium bicarbonate (2×50 ml), and brine (1×50 ml). The organic layer was then dried (MgSO4), filtered, and solvent removed. The residue so obtained was purified by column chromatography (ethylacetate:hexane=5:95). The yield of the pure product was 242 g (64%). CIMS: 379 (M+1).

Step 2: Phenylpropyl 2,3-O-(1-methylethylidene)-α-D-mannofuranoside:

Phenylpropyl 2,3;5,6-di-O-(1-methylethylidene)-α-D-mannofuranoside (50 g) was dissolved in aqueous acetic acid (200 ml) and the mixture heated at 60°–70° C. for 10 hours. The solvents were then stripped off and the residue dissolved in ether (500 ml), washed with aqueous sodium bicarbonate solution (2×50 ml), dried over MgSO4, filtered and the solvent removed. The crude product so obtained was purified using column chromatography (ethylacetate:hexane=5:95). The yield of the pure product was 39.3 g (88%) (5% of starting material was also recovered). CIMS: 339 (M+1).

Step 3: Phenylpropyl 2,3-O-(1-methylethylidene)-6-p-toluenesulfonyl-α-D-mannofuranoside:

A solution of p-toluenesulfonyl chloride (19:05 g; 0.1 mole) in anhydrous pyridine (100 ml) was added dropwise to a stirred solution of phenylpropyl 2,3-O-(1-methylethylidene)-α-D-mannofuranoside (33.8 g; 0.1 mole) in pyridine (100 ml), at 0°–5° C., over a period of 20 minutes the reaction mixture was stirred at the same temperature for 3 hours. Pyridine was then removed under diminished pressure at 40° C. and the residue extracted with ethylacetate (400 ml). The ethylacetate layer was washed with a saturated solution of sodium bicarbonate (2×75 ml), water (1×50 ml), brine (1×50 ml), organic layer dried over MgSO4, filtered and solvent removed. To the thick viscous oil was added 100 ml ether and cooled the flask in an ice bath. A white crystalline material formed was filtered and washed with 50 ml more of cold ether. The yield of the pure compound, m.p. 94°–95° C., was 85%. CIMS: 493 (M+1).

Step 4: Phenylpropyl 6-deoxy-2,3-O-(1-methylethylidene)-6-heptylamino-α-D-mannofuranoside:

A mixture of phenylpropyl 2,3-O-(1-methylethylidene)-6-p-toluenesulfonyl-α-D-mannofuranoside (4.92 g; 0.01 mole) and heptylamine (10 ml) was heated at 80°–85° C. for 2 hours. The reaction flask was then cooled to room temperature and added ether (30 ml). Solid salt formed was filtered and washed with 50 ml more of ether. The combined ether layer was washed with a saturated solution of sodium bicarbonate (2×10 ml), brine (1×10 ml) dried over MgSO4, filtered, and solvent removed. The residue so obtained was purified by column chromatography (ethylacetate:hexane=30:70). The yield of the pure product was 87%. CIMS: 436 (M+1).

EXAMPLE 16

Phenylpropyl 6-deoxy-2,3-O-(1-methylethylidene)-6-pyrrolidinyl-α-D-mannofuranoside:

This compound was prepared by reacting phenylpropyl 2,3-O-(1-methylethylidene)-6-p-toluenesulfonyl-α-D-mannofuranoside (4.92 g; 0.01 mole) with pyrrolidine (10 ml) by using the same procedure as described in Example 15. The crude product so obtained was purified by column chromatography (75% ether in hexane). The yield of the pure product was 89%. CIMS: 392 (M+1).

EXAMPLE 17

Phenylpropyl 6-deoxy-2,3-O-(1-methylethylidene)-6-1'-(3'-aminopropyl)pyrrolidinyl-α-D-mannofuranoside:

The title compound was obtained in 83% yield by reacting 6-tosyl compound with 1-(3-aminopropyl)pyrrolidine by employing the same procedure as described for example 15. CIMS: 449 (M+1).

EXAMPLE 18

Phenylpropyl 5,6-dideoxy-2,3-O-(1-methylethylidene)-5-heptylamino-β-L-gulofuranoside.

Step 1: Phenylpropyl 6-deoxy-2,3-O-(1-methylethylidene)-α-D mannofuranoside:

To a stirred suspension of lithium aluminum hydride (4.24 g) in dry THF (150 ml) was added a solution of Phenylpropyl 2,3-O-(1-methylethylidene)-6-p-toluenesulfonyl-α-D-Mannofuranoside (27.5 g) in dry THF (100 ml) dropwise at 0°–5° C. with vigorous stirring. After three hours, the excess LiAlH$_4$ was decomposed by careful addition of water (5 ml) followed by the addition of 15% aqueous NaOH (5 ml). It was then filtered through Celite, washed with 300 ml of ether. The combined filtrate was subjected to rotary evaporator to remove solvents. The residue was redissolved in ether (200 ml), washed with water (2×20 ml), ether layer dried (MgSO$_4$), filtered, and solvent removed. The product obtained (94% yield) was sufficiently pure and showed a single homogeneous spot on tlc. CIMS: 323 (M+1).

Step 2: Phenylpropyl 6-deoxy-2,3-O-(1-methylethylidene)-5-p-toluenesulfonyl-α-D-mannofuranoside:

p-Toluenesulfonylchloride (13 g; 2 equivalents) was added to a stirred solution of phenylpropyl 6-deoxy-2,3-O-(1-methylethylidene)-α-D-mannofuranoside (11 g) in pyridine (100 ml). The reaction mixture was stirred at room temperature for 24 hours. Pyridine was then stripped off under reduced pressure and worked up as usual with ethylacetate. The so solid product formed after the removal of the solvent was recrystallized from ether (75% yield) as a white crystalline material, m.p. 105°–106° C. (20% of starting material was recovered from the filtrate). CIMS: 477 (M+1).

Step 3: Phenylpropyl, 5,6-dideoxy-2,3-O-(1-methylethylidene)-5-heptylamino-β-L-gulofuranoside.

This reaction was carried out by treating phenylpropyl 6-deoxy-2,3-O-(1-methylethylidene)-5-p-toluenesulfonyl-α-D-mannofuranoside with heptylamine by exactly the same procedure as described for Step 4 of Example 15. The yield of the pure product was 73%. CIMS: 420 (M+1).

EXAMPLE 19

Phenylpropyl 5,6-dideoxy-2,3-O-(1-methylethylidene)-5-pyrrolidinyl-β-L-gulofuranoside:

The title compound was obtained in 79% yield by reacting phenylpropyl 6-deoxy-2,3-O-(1-methylethylidene)-5-p-toluenesulfonyl-α-D-mannofuranoside with pyrrolidine by exactly the same procedure as described for example 16. The product was purified by column chromatography using 25% ethylacetate in hexane. CIMS: 376 (M+1).

EXAMPLE 20

Phenylpropyl 5,6-dideoxy-2,3-O-(1-methylethylidene)-5-1'-(3'-aminopropyl)pyrrolidinyl-β-L-gulofuranoside:

This compound was obtained in 87% yield by treating 5-tosyl compound with 1-(3-aminopropyl)pyrrolidine by exactly the same procedure as described in example 18. CIMS: 418 (M+1).

EXAMPLE 21

Phenylpropyl 6-deoxy-2,3-O-(1-methylethylidene)-5-O-3'-(N',N'-dimethylamino-n-propyl)-α-D-mannofuranoside:

A mixture of phenylpropyl 6-deoxy-2,3-O-(1-methylethylidene)-α-D-mannofuranoside (3.22 g; 0.01 mole), solid potassium hydroxide (1.12 g; 0.02 mole) and dimethylaminopropylchloride) (1.46 g) was heated at 110° C. for 2.30 hours. The reaction flask was then cooled and added hexane (50 ml). It was filtered through celite and washed with 50 ml more of hexane. The removal of the solvent gave a crude product which was purified by column chromatography using 15% ethylacetate in hexane. The yield of the pure product was 96%. CIMS: 408 (M+1).

EXAMPLE 22

Phenylpropyl 6-deoxy-2,3-O-(1-methylethylidene)-5-O-(N'-ethyl)pyrrolidinyl-α-D-mannofuranoside:

The title product was obtained in 89% yield by reacting phenylpropyl 6-deoxy-2,3-O-(1-methylethylidene)-α-D-mannofuranoside (3.22 g), KOH (1.12 g) and chloroethyl pyrrolidine (1.2 equivalents) by exactly the same procedure as described in example 21. The product was purified by column chromatography (ethylacetate:hexane=5:95). CIMS: 420 (M+1).

EXAMPLE 23

2'-octyne 2,3-O-(1-methylethylidene)-α-D-mannofuranoside:

D-mannose (10 g) was suspended in acetous (100 ml) and added 2-octyne-1-ol (10 g) and a catalytic amount of concentrated sulfuric acid. The mixture was refluxed for 4 hours. After stripping off the solvents using rotary evaporation, the residue was dissolved in ethylacetate (200 ml), washed with sodium bicarbonate solution (2×20 ml), water (1×20 ml) and the organic layer dried over MgSO$_4$. It was then filtered and the filtrate subjected to rotary evaporator. The residue so obtained was purified by column chromatography using ethylacetate:hexane (5:95%) to yield the pure compound, 2'-octyne-2,3:5,6-di-O-(1-methylethylidene)-α-D-mannofuranoside, in 79% yield. This compound (2 g) was dissolved in 20 ml of aqueous acetic acid (60%) and heated the mixture at 50°–60° C. for 6 hours. The reaction was worked up as described earlier and purified by flask chromatography using 5% ether in hexane. The pure product, 2'-octyne 2,3-O-(1-methylethylidene)-α-D-mannofuranoside), was obtained in 79% yield. CIMS: 329 (M+1).

EXAMPLE 24

4'(1-Chlorobutyl) 2,3;5,6-di-O-(1-methylethylidene)-α-D-mannofuranoside.

A mixture of D-mannose (10 g), acetone (100 ml), 4-chloro-1-butanol (10 ml) and concentrated sulfuric acid (1 ml) was refluxed for 6 hours. TLC showed the reaction to be completed. The reaction flask was brought to ambient temperature and neutralized with triethylamine. The solvents were removed using rotary evaporator and the residue extracted with ether (200 ml), washed with a saturated solution of sodium bicarbonate (2×50 ml), water (1×50 ml), the organic layer dried (MgSO₄), filtered and solvent removed. The crude mixture so obtained was purified by column chromatography using 5% ethylacetate in hexane. The yield of the pure product was 81%.

Step 2: 4'-(1pyrrolidinyl)butyl 2,3:5,6di-O-(1-methylethylidene)-α-D-mannofuranoside:

A mixture of 4'-(1-chlorobutyl) 2,3:5,6-di-O-(1-methylethylidene)-α-D-mannofuranoside (5 g) and pyrrolidine (5 ml) was heated at 80°–85° C. for 2 hours. The excess pyrrolidine was then removed and the residue purified by column chromatography using ethylacetate:hexane (40:60). The yield of the product was 96%. CIMS: 386 (M+1).

Step 3: 4'-(1-pyrrolidinyl)butyl 2.3:-O-(1-methylethylidene)-α-D-mannofuranoside:

A solution of fully blocked compound obtained above in Step 2 (1 g) in 60% aqueous acetic acid (20 ml) was heated at 50°–60° C. for 6 hours. The solvents were then removed under reduced pressure and the residue dissolved in ethylacetate (50 ml), washed with sodium bicarbonate solution (2×10 ml), and with water (1×10 ml). The organic layer was then dried (MgSO₄), filtered and solvent removed. The product was purified by preparatory thin layer chromatography. The yield of the pure product was 88%. CIMS: 346 (M+1).

PHARMACOLOGICAL ACTIVITY

The compounds of the present invention have demonstrated immunomodulatory and anti-inflammatory effects in biological assays. Various standard in vitro assays have been performed on several of the compounds of the present invention to ascertain immunomodulatory and anti-proliferative activities. These include:

i Mixed lymphocyte response (MLR).
ii BUD-8 human cell line fibroblast proliferation assay.
iii Concanavalin A assay (the mouse spleen cell mitogen induced blastogenesis).

The MLR assay measures the effects of a study compound on the activation and antigen presentation of T-lymphocytes, therefore determining immunomodulatory properties. The mouse spleen cell mitogen-induced blastogenesis and the BUD-8 human fibroblast proliferation assays measure the effects of the the compounds of the present invention on cellular proliferation of cells involved in the pathogenesis of autoimmune diseases. These two assays are appropriate as screens to ascertain anti-inflammatory and/or autoimmune beneficial activity and are art accepted for such purposes.

The MLR is a classical assay used to measure T cell function by studying the proliferation response of T cells which are activated in vitro by genetically disparate stimulator cells. This is accomplished by co-culturing spleen cells from two different strains of mice. Splenic T cell proliferation occurs as a result of cellular activation signals generated by the ongoing cellular interactions.

In performing MLR assays, BALB/cBYJ mice were euthanized by cervical dislocation and their spleens removed. Single cell suspensions were prepared in culture medium (RPMI-1640 with hepes supplemented with 10% calf serum, 2 mM glutamine, 500 units penicillin/streptomycin, and $4\times10^{-5}$M 2-mercaptoethanol) using a Teflon pestle. The cells were centrifuged at 1500 RPM and the pellets resuspended in ACT (0.15M Tris, 0.14M ammonium chloride, pH 7.2) in order to lyse the red blood cells. After a 5 minute incubation at 37° C. in a waterbath, the cells were washed and resuspended in culture medium. The splenic lymphocytes were counted. C57BL/6J spleen cells, which were used as stimulator cells, were prepared in the same way. The stimulator cells were treated with 50 μg/ml of mitomycin C for 20 minutes at 37° C., then washed five times in culture medium. The proliferative response were measured by culturing $5\times10^5$ responder spleen cells with $5\times10$ stimulator cells in 96-well microtiter plates in the presence or absence of test article or vehicle (DMSO). Syngeneic control cultures using mitomycin C treated normal BALB/c spleen cells as the stimulator cells were also run. All cultures were run in triplicate.

Solutions of compounds of the present invention in DMSO were prepared at a stock concentration of 300 mM. Solutions were made in a culture medium to a concentration of 1, 10, 30, 100, and 300 μM. The vehicle DMSO was used as a negative control.

After incubation for 5 days at 37° C. with 5% carbon dioxide, the amount of cell proliferation was measured by adding 20 μl of MTT (10 mg/ml in PBS) (3-[4,5-dimethylthiazol-2-yl]-2,5-diphenyl-tetrazolium bromide) to each well. Plates were incubated for 4 hours at 37° C., after which 180 μl of supernatant was removed and 180 μl of 10% SDS in PBS was added. After an overnight incubation, the optical density (OD) of each well was read on a Molecular Devices microplate reader at 570–650 nm.

The results were determined by calculating the difference between the means of the allogeneic cultures and the means of the syngeneic cultures for each test compound concentration. Differences of the test article groups were compared to the difference of the control group. The percent change from the control was determined and an IC₅₀ estimated. The criteria used to establish activity levels were:

| Estimated IC$_{50}$ | |
| --- | --- |
| Inactive: | $\geq$300 μM |
| Weak: | $\geq$100 but <300 μM |
| Moderate: | $\geq$30 but <100 μM |
| Strong: | <30 μM |

Sixteen (16) novel compounds were assayed for their ability to modulate a Mixed Lymphocyte Response in vitro. The test compounds were added to MLR cultures to give final concentrations of 1, 10, 30, 100, and 300 μM. The responses observed in the test article treated wells were compared to the control wells. DMSO did not appear to have any effect on the response. The results for the test compounds are shown in Table 1. Based on the estimated IC$_{50}$, all the test compounds were strong inhibitors of the MLR.

A second assay was conducted to demonstrate inhibitory activity of the compounds of the present invention to the in vitro proliferation of human skin cells in tissue culture. The skin cell fibroblast line, BUD-8, was originally derived from the normal skin of a 56 year old white female and can now be obtained from the American Type Culture Collection, Rockville, Md. The concentration of the compounds which were used in this assay were: 1, 10, 30, 100, and 300 μM. The vehicle was used as the negative control. Test compounds were prepared in DMSO at a stock concentration of 300 mM. Appropriate dilutions were made in culture medium.

In this assay BUD-8 cells were collected, counted, and diluted to $2\times10^4$ cells/ml. 0.1 ml was plated per well to give 2×10³ cells/well. The compounds of the present invention were diluted in culture medium to the appropriate concentrations. Aliquates of 100 µl were distributed to triplicate wells. Control wells with vehicle and wells with media were also run. After a three day incubation at 37° C. with 5% carbon dioxide, proliferation was measured by adding 20 µl of MTT (10 mg/ml in PBS) (3-[4,5-dimethyl thiazol-2-yl]-2,5-diphenyl-tetrazolium bromide) to each well. Plates were incubated for 4 hours at 37° C., after which 180 µl of 10% SDS in PBS were added. After an overnight incubation, the optical density (OD) of each well was read using a Molecular Devices microplate reader at 570–650 nm.

Duplicate cultures were also set up to measure viability. After 3 days of incubation, supernatants were assayed for lactate dehydrogenase (LDH) activity to determine the viability of the cells, which is an indication of the toxicity of the test article on the BUD-8 cells. 0.1 ml of supernatent was mixed with 0.1 ml of the LDH substrate mixture which contains $5.4\times10^{-2}$M L(+) lactate, $6.6\times10^{-4}$M 2-p-iodophenyl-3-p-nitrophenyl tetrazolium chloride, $2.8\times10^{-4}$M phenazine methosulfate, $1.3\times10^{-3}$M NAD, and 0.2M Tris buffer. pH 8.2. Plates were read immediately for 5 minutes at 490 nm using a Molecular Devices microplate reader.

The mean for each test article treated group was determined and compared to the mean of the control group. The percent change from the control was calculated, and the IC$_{50}$ estimated. The criteria used to establish activity levels were:

| Estimated IC$_{50}$ | |
|---|---|
| Inactive: | $\geq 300$ µM |
| Weak: | $\geq 100$ but $<300$ µM |
| Moderate: | $\geq 30$ but $<100$ µM |
| Strong: | $<30$ µM |

Sixteen (16) test articles were assayed for their ability to inhibit fibroblast proliferation. The test article were added to BUD-8 cell cultures to give final concentrations of 1, 10, 30, 100, and 300 µM. The proliferation observed in the test article treated wells were compared to the DMSO control wells. The results of the test articles are shown in Table 1.

A third assay was conducted to demonstrate the ability of the compounds of the present invention to modulate T-lymphocyte activity. It is known that the induction and maintenance of most inflammatory diseases are typically due to the unrestricted activity of T-lymphocytes. Therefore, it is advantageous to identify compounds which are modulators of T-lymphocyte activity for eventual use in the regulation of inflammatory diseases, including acquired immune deficiency syndrome, psoriasis, systemic lupus, erythromatosus, and rheumatoid arthritis.

A simple method is used to screen compounds for their ability to modulate T-lymphocyte activity which comprises assessing the capacity of the compounds to alter the activation of murine spleen cells in response to T-lymphocyte mitogen activators, such as Conconavalin-A (Con-A). The method used to measure the effects of the compounds of the present invention on the blastogenic response of spleen cells to the T-lymphocyte mitogen (Con-A) is as follows:

The response of a mouse spleen cells to the T cell mitogen Con-A is a classical assay. In this assay, mice were euthanized by cervical dislocation and their spleens removed surgically. A single cell suspension of the spleens was prepared in culture medium (RPMI-1640 with hepes, supplemented with 10% calf serum, 2 mM glutamine, 500 units penicillin/streptomycin, and $4\times10^{-5}$M 2-mercaptoethanol) using a Teflon pestle. The cells were centrifuged at 1500 RPM and the pellets resuspended in ACT (0.15M Tris, 0.14M Ammonium chloride, pH 7.2) in orde to lyse the red blood cells. After a five minutes incubation in a 37° C. waterbath, the cells were washed and resuspended in culture medium. The splenic lymphocytes were counted using an electronic Coulter Counter and diluted to $5.0\times10^6$ cells/ml.

The test articles were diluted in culture medium to the appropriate concentrations. 100 µl aliquots were distributed to triplicate wells in a 96-well microtiter plate. 50 µl of lymphocytes ($2.5\times10^5$ cells) were added to each well. Control wells with vehicle and wells with media were also run. Plates were incubated for one hour at 37° C. 50 µl of Con-A (5 µl/ml) were then added to the wells to result in a final concentration of 1.25 µg/ml. After incubation at 37° C. with 5% carbon dioxide for 3 days, proliferation was measured by adding 20 µl of MTT (10 mg/mlin PBS) [3-(4,5-dimethyl-thiazol-2-yl)-2,5-diphenyl tetrazolium bromide] to each well. Plates were incubated for 4 hours at 37° C., after which 180 µl of 10% SDS in PBS were added. After an overnight incubation, the optical density (OD) of each well was read using a Molecular Devices microplate reader at 570–650 nm.

Duplicate cultures without Con-A were also set up. After 3 days of incubation, supernatants were assayed for lactate dehydrogenase activity to determine the viability of the cells, which is an indication of the toxicity of the test article on the splenic lymphocytes. 0.1 ml of supernatant was mixed with 0.1 ml of the LDH substrate mixture which contains $5.4\times10^{-2}$M L(+) lactate, $6.6\times10^{-4}$M 2-p-iodophenyl-3-p-nitrophenyl tetrazolium chloride, $2.8\times10^{-4}$M phenazine methosulfate, $1.3\times10^{-3}$M NAD, and 0.2M Tris buffer, pH 8.2. Plates were read immediately for 5 minutes at 490 nm using a Molecular Devices microplate reader.

The mean for each test article treated group was determined and compared to the mean of the control group. The percent change from the control was calculated, and the IC$_{50}$ was estimated.

The criteria used to establish activity levels were:

| Estimated IC$_{50}$ | |
|---|---|
| Inactive: | $\geq 300$ µM |
| Weak: | $\geq 100$ but $<300$ µM |
| Moderate: | $\geq 30$ but $<100$ µM |
| Strong: | $<30$ µM |

Sixteen (16) test articles were assayed for their ability to modulate a Con-A response in vitro. The test article were added to Con-A cultures to give a final concentrations of 1, 10, 30, 100, and 300 µM. The response observed in the test article treated wells were compared to the control wells. DMSO alone had little effect on the response. The results for the test articles are shown in Table 1.

The compounds of the present invention were also tested against various tumor cell lines, derived from seven cancer types. These include leukemia, melanoma, lung cancer, colon cancer, renal cancer, ovarian cancer, and brain cancer. Most of the compounds have shown significant activity in various screens, particularly against colon cancer and melanoma. The results of the test articles (Average GI$_{50}$) are shown in Table 1.

The compounds of the present invention have demonstrated significant immunomodulatory and antiproliferative properties when tested in the aforementioned in vitro assays. The concentration tested ranged from 1 μM to 300 μM, with the most efficacious activities defined as one-half the maximal inhibitory concentrations (IC$_{50}$) or (GI$_{50}$) of 30 μM or less.

TABLE

| Compound # | IC$_{50}$ (μM) | | | GI (μM) |
| | MLR | Con A | Fibroblast | Log 10 values |
|---|---|---|---|---|
| 3. | <1 | 3.3 | 18 | −5.04 |
| 4. | 27 | 2.7 | 35 | |
| 5. | 19 | 17 | >200 | |
| 6. | <0.5 | 3.2 | 38 | |
| 7. | 0.75 | 2.9 | 105 | |
| 8. | <1 | 17 | 16 | −5.64 |
| 10. | <1 | 3 | 17 | −4.94 |
| 12. | <0.5 | 3.2 | 42 | |
| 15. | 0.99 | 2.8 | 170 | |
| 20. | <1 | 59 | >300 | −4.06 |
| 21. | <1 | 7 | 19 | −5.13 |
| 22. | 0.85 | 2.5 | 16 | |
| 24. | <1 | 28 | 225 | −4.02 |
| 26. | <1 | 18 | 65 | −4.23 |
| 27. | 5.8 | <3 | 148 | |
| 29. | 26 | 49 | 190 | |

While the present invention has been described in terms of its specific embodiments, certain modifications and equivalents will be apparent to those skilled in the art and are intended to be included within the scope of the present invention, which is to be limited only by scope of the appended claims.

What is claimed as new and desired to be secured by Letters Patent of the United States is:

1. A compound selected from the group consisting of:
   n-Nonyloxypropyl 2,3-O-(1-methylethylidene)-6-deoxy-6-pyrrolidinyl-α-D-mannofuranoside,
   n-Nonyloxypropyl 2,3-O-(1-methylethylidene)-6-deoxy-6-piperidinyl-α-D-mannofuranoside,
   n-Nonyloxypropyl 2,3-O-(1-methylethylidene)-6-deoxy-6-morpholinyl-α-D-mannofuranoside,
   n-Nonyloxypropyl 2,3-O-(1-methylethylidene)-6-deoxy-6-hexamethyleneimino-α-D-mannofuranoside,
   n-Nonyloxypropyl 2,3-O-(1-methylethylidene)-6-deoxy-6-aminoethylpyrrolidinyl-α-D-mannofuranoside,
   n-Nonyloxypropyl 2,3-O-(1-methylethylidene)-6-deoxy-5-O-(N,N-dimethylaminopropyl)-α-D-mannofuranoside,
   n-Nonyloxypropyl 2,3-O-(1-methylethylidene)-6-deoxy-5-O-hexamethyleneiminoethyl-α-D-mannofuranoside,
   n-Nonyloxypropyl 2,3-O-(1-methylethylidene)-6-deoxy-5-O-(N'-ethylpyrrolidinyl)-α-D-mannofuranoside,
   n-Nonyloxypropyl 2,3-O-(1-methylethylidene)-6-deoxy-5-O-(N'-ethylpiperidinyl)-α-D-mannofuranoside,
   n-Nonyloxypropyl 5,6-dideoxy-2,3-O-(1-methylethylidene)-5-pyrrolidinyl-β-L-gulofuranoside,
   Phenylpropyl 6-deoxy-2,3-O-(1-methylethylidene)-6-pyrrolidinyl-α-D-mannofuranoside,
   Phenylpropyl 6-deoxy-2,3-O-(1-methylethylidene)-6-aminopropylpyrrolidinyl-α-D-mannofuranoside,
   Phenylpropyl 5,6-dideoxy-2,3-O-(1-methylethylidene)-5-pyrrolidinyl-β-L-gulofuranoside,
   Phenylpropyl 5,6-dideoxy-2,3-O-(1-methylethylidene)-5-aminoethylpyrrolidinyl-β-L-gulofuranoside,
   Phenylpropyl 6-deoxy-2,3-O-(1-methylethylidene)-5-O-3$^1$-(N$^1$N$^1$-dimethylamino-n-propyl)-α-D-mannofuranoside,
   Phenylpropyl 6-deoxy-2,3-O-(1-methylethylidene)-5-O-(N'-ethylpyrrolidinyl)-α-D-mannofuranoside,
   2'-Octyne 2,3-O-(1-methylethylidene)-α-D-mannofuranoside and
   4'-(1-Pyrrolidinyl)butyl 2,3-O-(1-methylethylidene)-α-D-mannofuranoside.

2. A pharmaceutical composition for the treatment of inflammatory and/or autoimmune disorders comprising an effective amount of a compound of claim 1, or a physiologically acceptable acid-addition salt thereof and a pharmaceutically acceptable carrier.

3. A method of treating an animal or human suffering from an inflammatory disorder which comprises administering thereto an effective amount of a compound of claim 1 or a physiologically acceptable acid-addition salt thereof.

4. A method of treating an animal or human suffering from an autoimmune disorder which comprises administering thereto an effective amount of a compound of claim 1 or a physiologically acceptable acid-addition salt thereof.

5. The method of claim 4, wherein the compound is administered orally or parentally.

6. A compound according to claim 1, selected from the group consisting of n-Nonyloxypropyl 2,3-O-(1-methylethylidene)-6-deoxy-6-pyrrolidinyl-α-D-mannofuranoside and Phenylpropyl 6-deoxy-2,3-O-(1-methylethylidene)-5-O-3$^1$-(N$^1$N$^1$-dimethylamino-n-propyl)-α-D-mannofuranoside.

7. n-Nonyloxypropyl 2,3-(1-methylethylidene)-6-deoxy-6-aminopropylpyrrolinyl-α-D-mannofuranoside.

8. A compound according to claim 1, selected from the group consisting of n-Nonyloxypropyl 2,3-O-(1-methylethylidene)-6-deoxy-6-pyrrolidinyl-α-D-mannofuranoside, n-Nonyloxypropyl 2,3-O-(1-methylethylidene)-6-deoxyaminoethylpyrrolidinyl-α-D-mannofuranoside, n-Nonyloxypropyl 2,3-O-(1-methylethylidene)-6-deoxy-5-O-(N$^1$-ethylpyrrolidinyl)-α-D-mannofuranoside, Phenylpropyl 6-deoxy-2,3-O-(1-methylethylidene)-6-aminopropylpyrrolidinyl-α-D-mannofuranoside, Phenylpropyl 6-deoxy-2,3-O-(1-methylethylidene)-5-O-(N$^1$-ethylpyrrolidinyl)-α-D-mannofuranoside and 4'-(1-Pyrrolidinyl)butyl 2,3-O-(1-methylethylidene)-α-D-mannofuranoside.

* * * * *